July 7, 1964 F. W. ANDERSON Plant Pat. 2,418

PEACH TREE

Filed June 13, 1963

INVENTOR

Frederic W. Anderson

Webster & Webster

ATTYS.

United States Patent Office

Plant Pat. 2,418
Patented July 7, 1964

2,418
PEACH TREE

Frederic W. Anderson, Merced, Calif., assignor to L. E. Cooke Co., San Gabriel, Calif., a corporation Filed June 13, 1963, Ser. No. 287,728
1 Claim. (Cl. Plt.—43)

This invention is directed to a new and distinct variety of peach tree principally characterized by its small or dwarf size, and the bearing, by such tree, of substantially normal size, yellow fleshed, freestone fruit of acceptable quality; the variety being well adapted for growing both as an ornamental tree, and for the production of fruit for home and local market use.

The variety was originated by me, in my experimental orchard located near Merced, California, during a long term plant breeding project—spanning approximately ten years—the object of which was the origination of fruit trees, including peach trees, of such small or dwarf size that—in addition to ornamental value—pruning, thinning, and harvesting operations could be conducted without the use of ladders and by a person standing on the ground adjacent the tree.

The variety is a sib of and very similar in tree and fruit to the genetically dwarf Golden Prolific nectarine (United States Plant Patent No. 2,193) but is a peach; the variety having been originated by me, under close and careful observation, in the following manner:

The Flory dwarf peach (unpatented) was crossed with the Late Le Grand nectarine (United States Plant Patent No. 1,035), and the resultant seed all produced normal size peach trees which bore white fleshed peach fruit. In turn, seed from such trees produced about seventy-five percent normal size trees and twenty-five percent dwarf trees; some being peach trees and others nectarine trees. Of these last mentioned peach and nectarine trees, both those of normal and dwarf size, approximately three-fourths bore white fleshed fruit while the remaining one-fourth bore yellow fleshed fruit. The present variety is a selection of one of such dwarf peach trees whose fruit was yellow fleshed; the variety having been selected by me—for subsequent reproduction—upon the recognition of its commercial potential as a combination ornamental and fruit tree.

Subsequently, asexual reproduction of the variety was accomplished by me, in my experimental orchard located as aforesaid, by grafting on mature orchard trees; such reproductions having run true in all respects.

Figure 1:
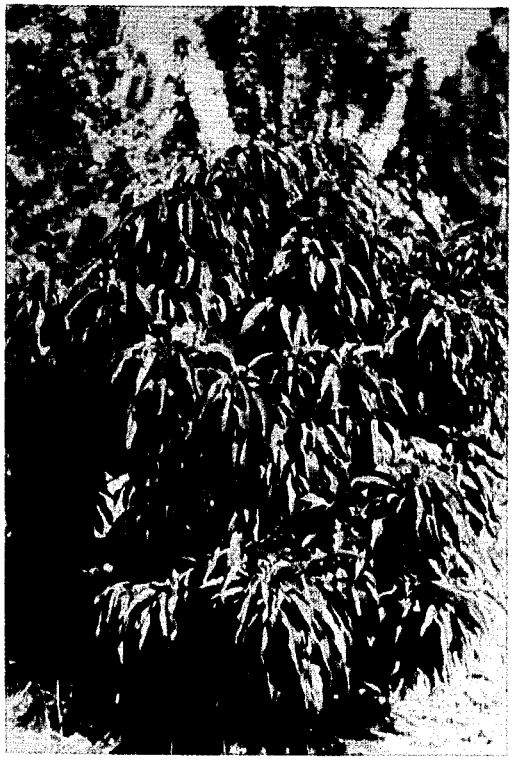
FIG. 1 is a view showing the tree in full leaf.
Figure 2:
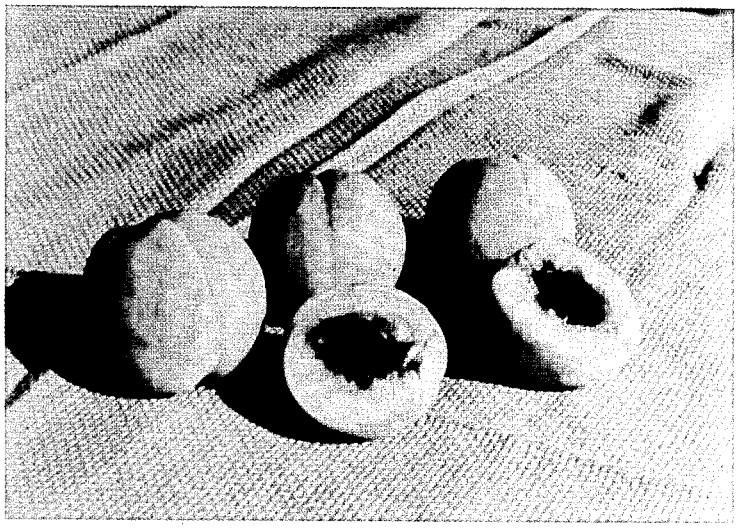
FIG. 2 is a view showing several of the fruits, one being cut into halves and with the stone remaining in one half.

Referring now specifically to this new and distinct variety of peach tree, the following is a detailed pomological description thereof in outline; all major color plate identifications being by reference to Maerz and Paul Dictionary of Color, except where common terms of color definition are employed.

Tree:
- *Size.*—Genetically dwarf. Average height—6–8 feet.
- *Vigor.*—Vigorous.
- *Form.*—Spreading.
- *Density.*—Dense.
- *Production.*—Productive.
- *Bearing.*—Regular bearer.

Trunk:
- *Size.*—Stocky.
- *Texture.*—Shaggy.

Branches:
- *Size.*—Stocky.
- *Texture.*—Shaggy.

Leaves:
- *Size.*—Large. Average length — 6". Average width—⅞".
- *Margin.*—Crenate.
- *Petiole.*—Short; medium thickness.
- *Glands.*—Average number and position—two to three on petiole and two or more on blade. Alternate; medium size; reniform.
- *Color.*—Top side—medium green (23–L–5). Under side—lighter green (22–K–6).

Flower buds:
- *Size.*—Medium.

Flowers:
- *Blooming period.*—March 5 to March 20, 1962. Medium as compared with other varieties.
- *Size.*—Large.
- *Fertility.*—Self-fertile, with red anthers.

Fruit:
- *Maturity when described.*—Eating ripe—August 25, 1962.
- *Date of first picking.*—August 21, 1962.
- *Date of last picking.*—August 30, 1962.
- *Size.*—Uniform; large. Average diameter axially—2⅝". Average transversely in suture plane—2 7/16".
- *Form.*—Uniform; symmetrical; globose to slightly oblate.
- *Suture.*—Distinct; extends from base to apex.
- *Ventral surface.*—Rounded slightly.
- *Cavity.*—Circular. Average depth—¼". Average breadth—⅜". Markings—red mottling.
- *Base.*—Truncate.
- *Apex.*—Depressed.

Skin:
- *Thickness.*—Medium.
- *Texture.*—Medium.
- *Tendency to crack.*—None noted.
- *Down.*—Moderate; medium length.
- *Color.*—Yellow (10–L–7 to 10–K–8), partially mottled orange-red (3–F–12 to 3–J–12).

Flesh:
- *Texture.*—Soft; melting.
- *Ripens.*—Even.
- *Flavor.*—Subacid to mild.
- *Eating quality.*—Fair to good.
- *Color.*—Yellow (9–L–6 to 9–K–8), with red (5–L–4) near stone. Surface of pit cavity—red, with yellow fibers.
- *Juice.*—Moderate.

Stone:
- *Type.*—Free.
- *Size.*—Medium. Average length—1 5/16". Average breadth—1 1/16". Average thickness—⅞".
- *Tendency to split.*—Slight.
- *Kernels.*—Bitter.

*Color.*—Brown (8–L–12).
Use: Home, and local market.
Keeping quality: Medium.
Shipping quality: Medium to poor; i.e. not firm enough for commercial long distance shipment.

The tree and its fruit herein described may vary in slight detail due to climatic and soil conditions under which this variety may be grown; the present description being of the variety as grown in the Central Valley of California.

The following is claimed:

A new and distinct variety of peach tree, as illustrated and described, characterized by its dwarf size, averaging six to eight feet in height; and further characterized by the productive bearing of large size, yellow fleshed freestone fruit having yellow skin partially mottled with orange red; the variety being a sib of and very similar to the Golden Prolific nectarine, but being a peach.

No references cited.